United States Patent
Yamazaki et al.

(10) Patent No.: US 7,214,222 B2
(45) Date of Patent: May 8, 2007

(54) LASER DEPILATING METHOD AND LASER DEPILATING APPARATUS

(75) Inventors: Iwao Yamazaki, Tokyo (JP); Yoshihiro Izawa, Yachiyo (JP); Akitsugu Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 10/470,333

(22) PCT Filed: Jan. 29, 2002

(86) PCT No.: PCT/JP02/00622

§ 371 (c)(1),
(2), (4) Date: Jul. 28, 2003

(87) PCT Pub. No.: WO02/060531

PCT Pub. Date: Aug. 8, 2002

(65) Prior Publication Data

US 2004/0065846 A1    Apr. 8, 2004

(30) Foreign Application Priority Data

Jan. 29, 2001 (JP) .............................. 2001-019941
Jan. 29, 2001 (JP) .............................. 2001-019942

(51) Int. Cl.
*A61B 18/18* (2006.01)
*A61B 18/22* (2006.01)

(52) U.S. Cl. .............................. 606/9; 606/10; 606/11; 607/89

(58) Field of Classification Search ............ 606/3, 606/9–12, 131; 607/88–91
See application file for complete search history.

(56) References Cited

U.S. PATENT DOCUMENTS

| 5,843,072 A | * | 12/1998 | Furumoto et al. | 606/9 |
| 6,149,644 A | * | 11/2000 | Xie | 606/9 |
| 6,162,211 A | * | 12/2000 | Tankovich et al. | 609/9 |

(Continued)

FOREIGN PATENT DOCUMENTS

EP    1 031 324 A1    8/2000

(Continued)

OTHER PUBLICATIONS

English Translation of International Preliminary Examination Report, dated Mar. 5, 2003, in International Application No. PCT/JP02/00622.

(Continued)

*Primary Examiner*—A. Farah
(74) *Attorney, Agent, or Firm*—Finnegan, Henderson, Farabow, Garrett & Dunner, L.L.P.

(57) ABSTRACT

A laser depilating method for depilating treatment by irradiating a skin surface with a laser beam emitted from a semiconductor laser. A treatment region of the skin surface is treated with a semiconductor laser beam for an irradiation time of 100 msec or more per irradiation while controlling the laser beam so that the energy density when irradiating the skin surface may be in a range of 0.01–1 $J/mm^2$. Irradiation of the skin surface with a semiconductor laser beam under such a condition provides a more secure and efficient treatment effect of laser depilation. A plurality of semiconductor laser beams are used as necessary to irradiate a wider area of skin surface at a time.

12 Claims, 7 Drawing Sheets

U.S. PATENT DOCUMENTS

| | | | |
|---|---|---|---|
| 6,610,052 B2 * | 8/2003 | Furumoto | 606/9 |
| 6,641,578 B2 * | 11/2003 | Mukai | 606/9 |
| 6,663,659 B2 * | 12/2003 | McDaniel | 606/9 |
| 6,695,835 B2 * | 2/2004 | Furuno et al. | 606/9 |
| 6,736,807 B2 * | 5/2004 | Yamazaki et al. | 606/9 |

FOREIGN PATENT DOCUMENTS

| | | |
|---|---|---|
| JP | 2000-217938 | 8/2000 |
| JP | 2000-245525 | 9/2000 |
| JP | 2000-245767 | 9/2000 |
| JP | 2001-500529 | 1/2001 |
| JP | 2001-046141 | 2/2001 |
| JP | 2001-161836 | 6/2001 |
| JP | 2000-201726 | 7/2002 |
| WO | WO 96/23447 | 8/1996 |
| WO | WO/98/48716 | 11/1998 |
| WO | WO 99/43264 | 9/1999 |
| WO | WO 00/32121 | 6/2000 |
| WO | WO 00/56240 | 9/2000 |

OTHER PUBLICATIONS

Supplemental Partial European Search Report, issued by European Patent Office, dated Jan. 31, 2005, for European Application No. 02 71 6430.

* cited by examiner

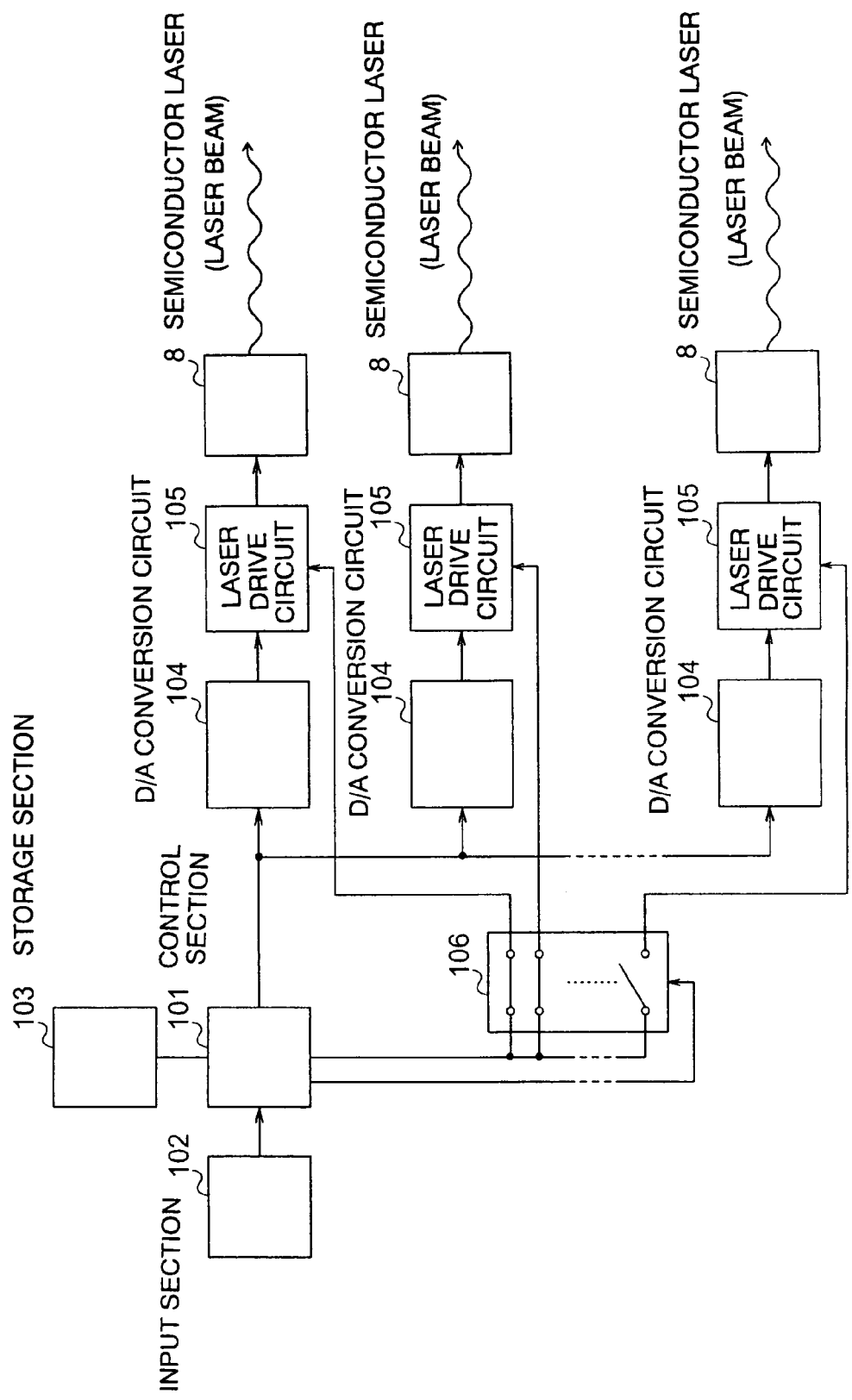

LASER DEPILATING METHOD AND LASER DEPILATING APPARATUS

TECHNICAL FIELD

The present invention relates to a laser depilating method and a laser depilating apparatus for depilating treatment with a laser beam from a semiconductor laser.

BACKGROUND ART

A conventional body hair depilating treatment (treatment for retarding or lowering the regrowth of hair) was performed by burning out hair roots by an electrical needle. This treating method must treat hair one by one, taking a very long treating time and causing pain during treatment. Therefore, a laser depilating treatment is now being used instead of the depilating treatment using the electrical needle.

The laser depilating treatment is a treatment which retards the regrowth (growth) of hair by giving thermal or physical damage to a germinative cell and hair papilla of a hair bulb at the hair root and also to a bulge and a sebaceous gland with a laser beam. For the conventional laser depilating treatment, various types of laser irradiation devices such as a YAG laser (oscillation wavelength: approximately 1064 nm), a ruby laser (oscillation wavelength: approximately 694 nm), an alexandrite laser (oscillation wavelength: approximately 755 nm) and a semiconductor laser (oscillation wavelength: approximately 800 nm) as described in, for example, Japanese National Stage Laid-Open Publication No. 2001-500529 (International Publication No. WO98/48716) are used.

Among them, a depilating treatment apparatus using the YAG laser or the ruby laser is an apparatus which irradiates a skin surface with a high power laser beam to directly destroy (e.g., thermolysis) a hair root, a germinative cell and the like. A laser beam of the YAG laser or the like has a long wavelength and poor absorption efficiency by melanin in a hair root and germinative cell, and its power is high, so that its irradiation time per irradiation is limited. Besides, the depilating treatment apparatus using the YAG laser utilizes a very expensive medical laser irradiation device, and the depilating treatment must be performed as medical treatment.

Meanwhile, a laser depilating apparatus using a small and inexpensive semiconductor laser (laser diode) has a low power (e.g., approximately 0.01 to 10 W) laser beam emitted from the semiconductor laser, so that the laser depilating treatment can be performed as cosmetic treatment. The semiconductor laser beam has a wavelength of, for example, approximately 780 to 810 nm. This laser beam having such a wavelength is hardly absorbed by water or blood but has very high absorption efficiency by melanin in a hair root (hair shaft) and a germinative cell. Thus, the regrowth (growth) of hair can be retarded efficiently by thermal energy of the laser beam absorbed by the melanin.

As described above, the laser depilating apparatus using the semiconductor laser has a feature that the semiconductor laser beam has a wavelength suitable for the depilating treatment. However, the conventional laser depilating apparatus does not have an irradiation time, irradiation energy and other various kinds of conditions for irradiation of the semiconductor laser beam examined adequately or decided, so that an adequate depilating effect cannot be obtained depending on the situation or hair is reversely grown.

For example, Japanese Patent Unexamined Publication No. 2000-201726 describes a laser depilating apparatus which is comprised of a semiconductor laser having light power of 5 to 1000 mW, light power adjusting means for adjusting the light power of the laser beam emitted from the semiconductor laser, and irradiation time setting means for setting an irradiation time of the laser beam. Here, the light power of the laser beam is adjusted by the on-time of the laser pulse, so that thermal energy based on the irradiation of the laser beam might not be conducted effectively to the entire hair follicle tissue. Besides, there is no suggestion about an energy density or the like of the laser beam effective for the depilating treatment.

Japanese Patent Unexamined Publication No. 2001-46141 describes a laser depilating apparatus which is comprised of a laser diode for irradiating a laser beam, a control section for controlling an irradiation time of the laser beam and an output control circuit for adjusting a voltage or a current applied to the laser diode. But, the above publication does not describe specific power of the laser beam (semiconductor laser beam), an irradiation time or an energy density of the laser beam effective for depilating treatment.

Japanese Patent Unexamined Publication No. 2000-245525 describes laser therapy equipment using an alexandrite laser (oscillation wavelength: approximately 755 nm) having a wavelength similar to that of the semiconductor laser. Here, it is shown that the laser beam power is generally in a range of 10 to 40 J/cm$^2$ (0.1 to 0.4 J/mm$^2$). However, the alexandrite laser has the same high power as the YAG laser does, so that its laser irradiation time is limited to 10 to 40 msec. Besides, the high power alexandrite laser directly destroys (cauterizes) a hair root and the like in the same way as the YAG laser to perform the depilating treatment, so that the depilating treatment cannot be performed by conducting the thermal energy of the laser beam to the entire hair follicle tissue like the semiconductor laser.

In addition, the conventional laser depilating apparatus is difficult to increase an irradiated area per treatment with the laser beam while keeping the energy density effective for depilating. Japanese Patent Unexamined Publication No. 2000-217938 describes a laser depilating apparatus having a plurality of semiconductor lasers (laser diodes) which are circularly disposed. By using the plurality of semiconductor lasers, an irradiation area of the laser beam is increased. But, the plurality of semiconductor lasers circularly disposed are limited from increasing the irradiation area of the laser beam, and if the irradiation area is excessively increased, the laser beam might have a nonuniform energy density.

Therefore, it is desired to increase an irradiation area of the semiconductor laser beam so to improve the depilating effect of the semiconductor laser beam. There is some consideration being made on disposition of many laser diode elements in an array shape to use a semiconductor laser having high power equivalent to that of the YAG laser. But, such a laser irradiation device has variations in power density because the laser beams emitted from the individual diode elements cause interference with each other. And, because the semiconductor laser beam is designed to have high power, the feature of the semiconductor laser beam that the absorption efficiency by melanin is high cannot be utilized fully.

The present invention is to provide a laser depilating method and laser depilating apparatus which can provide a laser depilating effect more securely and efficiently by utilizing the feature of the semiconductor laser beam that the absorption efficiency by melanin in hair shafts and germinative cells is high. Besides, it also provides a laser depilating apparatus having a treatment region increased and a treatment speed improved while keeping the depilating effect of the semiconductor laser beam.

DISCLOSURE OF THE INVENTION

The laser depilating method of the present invention is a laser depilating method for depilating treatment by irradiating a skin surface with a laser beam emitted from a semiconductor laser, comprising irradiating a treatment region of the skin surface with the laser beam for an irradiation time of 100 msec or more per irradiation while controlling an energy density to a range of 0.01 to 1 $J/mm^2$ when the skin surface is irradiated with the laser beam; and performing the depilating treatment by transmitting thermal energy based on the irradiation of the laser beam to the entire hair follicle tissue of the treatment region. In the laser depilating method of the invention, the laser beam (a semiconductor laser beam) emitted from the semiconductor laser has a wavelength in a range of, for example, 750 to 900 nm.

The laser depilating apparatus of the invention is a laser depilating apparatus, comprising a semiconductor laser for emitting a laser beam having a wavelength in a range of 750 to 900 nm; a radiating head having a light path for guiding the laser beam and a laser irradiation surface so to irradiate a skin surface subject to depilating treatment with the laser beam emitted from the semiconductor laser; an irradiation condition control section for controlling an energy density to a range of 0.01 to 1 $J/mm^2$ when the skin surface is irradiated with the laser beam while keeping the irradiation time of the laser beam at 100 msec or more per irradiation.

According to the present invention, the irradiation time per irradiation (one time) of the semiconductor laser beam having the above-described wavelength is controlled to 100 msec or more. Thus, it becomes possible to effectively and efficiently use the thermal energy of the semiconductor laser beam. In other words, when the irradiation time of the semiconductor laser beam is set to 100 msec or more, the thermal energy of the semiconductor laser beam absorbed by melanin in the hair shafts and germinative cells can be conducted to the entire hair follicle tissue (hair bulb, hair shaft, and connective tissue including sheath, bulge, sebaceous gland and the like around the hair shaft). The thermal damage is securely and efficiently applied to the entire hair follicle tissue to exert an influence on the regrowth of hair, so that the regrowth of hair can be retarded without fail.

Even if the irradiation time per irradiation of the semiconductor laser beam is simply extended, the thermal energy becomes insufficient and the thermal damage cannot be applied efficiently to the entire hair follicle tissue if an energy density is insufficient when the semiconductor laser beam is irradiated to a skin surface. Therefore, to obtain the hair regrowth retarding effect with reliability, the energy density of the semiconductor laser beam is controlled to a range of 0.01 to 1 $J/mm^2$. By using the semiconductor laser beam having the above energy density, the thermal energy having a high depilating effect can be conveyed securely and efficiently to the entire hair follicle tissue.

The laser depilating apparatus of the invention is further comprised of the semiconductor laser in plural numbers; and an optical system for gathering a plurality of laser beams emitted from the plurality of semiconductor lasers and forming so that the entire region of the laser irradiation surface of the radiation head is substantially irradiated with the laser beams. The radiating head has, for example, a rectangular laser irradiation surface, and the plurality of semiconductor lasers are disposed so that the plurality of laser beams irradiate substantially different regions in the rectangular laser irradiation surface.

By the laser depilating apparatus provided with the plurality of semiconductor lasers, the semiconductor laser beams having a substantially constant power density can be collectively irradiated to a wide rang of skin surface. The depilating treatment can be performed on a wide range by a single laser irradiation by increasing an irradiation range (irradiation area) of the semiconductor laser beam. Therefore, a treating speed can be increased substantially without degrading the depilating effect by the semiconductor laser beam.

BRIEF DESCRIPTION OF THE DRAWINGS

FIG. 9 is a block diagram showing a structure of a drive control section of a semiconductor laser of the laser depilating apparatus according to another embodiment of the present invention.

BEST MODE FOR CARRYING OUT THE INVENTION

Modes for practicing the present invention will be described.

Figure 1:
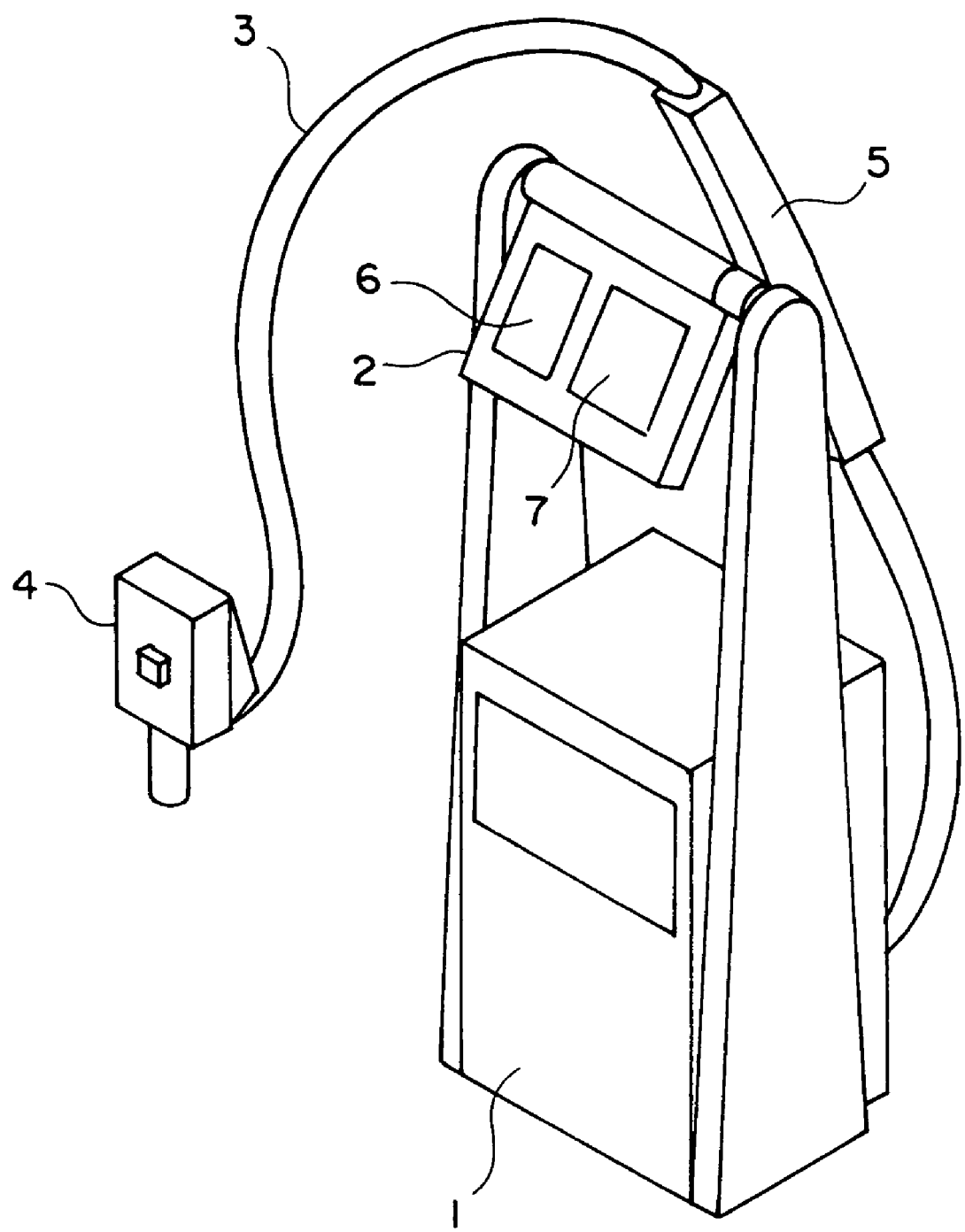
FIG. 1 is a perspective view schematically showing a general structure of the laser depilating apparatus according to an embodiment of the present invention.

FIG. 1 is a perspective view schematically showing a general structure of the laser depilating apparatus according to an embodiment of the present invention. In the drawing, 1 is a laser depilating apparatus body having an operation panel 2, and the apparatus body 1 has therein a main power supply, a semiconductor laser power supply, a control circuit for controlling the drive of a semiconductor laser, the operation of a compressor and the like, a circuit for a confirmation screen, and the like.

A laser radiating probe 4 is connected to the laser depilating apparatus body 1 through a cable 3. The laser radiating probe 4 is configured to be freely movable by an angle adjusting arm 5. The cable 3 contains therein lead wires for connecting the semiconductor laser power supply of the apparatus body 1 and between the control circuit and the laser radiating probe 4, an air tube for supplying air from the compressor to the laser radiating probe 4, and the like.

The laser depilating apparatus body 1 has a CCD camera-mounted confirmation probe which is not shown. Laser depilating treatment can be performed while checking a skin surface with an image taken by the CCD camera of the confirmation probe. The image taken by the CCD camera is shown on a color liquid crystal screen 6 of the operation panel 2. On the operation panel 2, a touch-sensitive operation screen 7, a main power switch (not shown) and the like are disposed.

Figure 2:
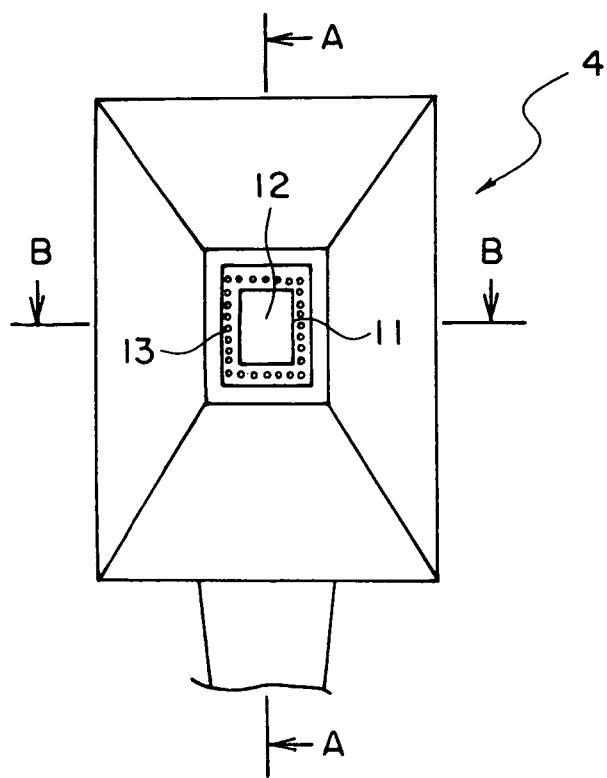
FIG. 2 is a front view showing a laser radiating probe of the laser depilating apparatus of FIG. 1.
Figure 3:
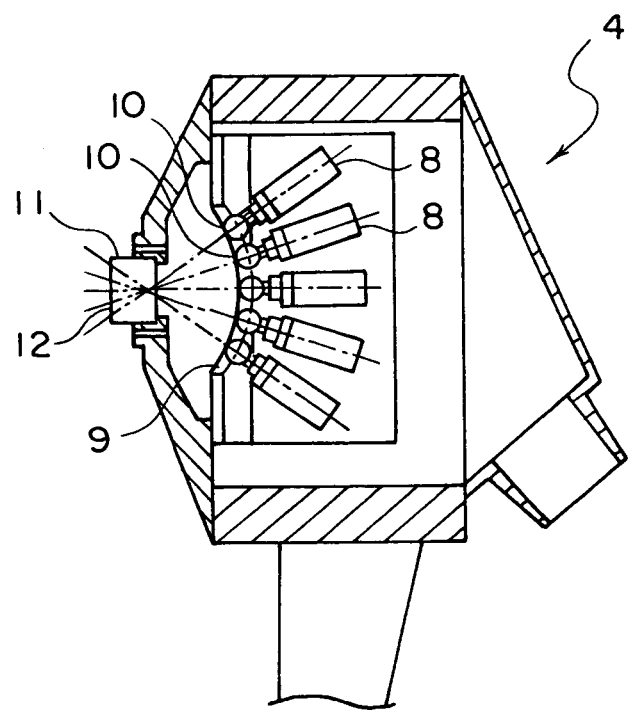
FIG. 3 is a vertical sectional view taken along line A—A of the laser radiating probe shown in FIG. 2.
Figure 4:
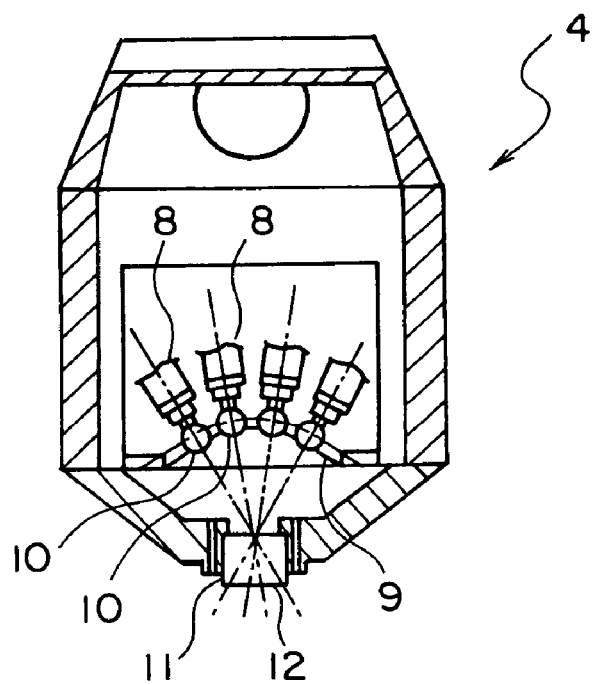
FIG. 4 is a transverse sectional view taken along line B—B of the laser radiating probe shown in FIG. 2.

FIG. 2, FIG. 3 and FIG. 4 are views showing a structure of the laser radiating probe 4. FIG. 2 is a front view of the laser radiating probe 4, FIG. 3 is a vertical sectional view taken along line A—A of FIG. 2, and FIG. 4 is a transverse sectional view taken along line B—B of FIG. 2. As shown in these drawings, a plurality of semiconductor lasers 8, 8 . . . are disposed as a laser source within the laser radiating probe 4. The number of semiconductor lasers 8 is not limited to be multiple, but a single semiconductor laser can be used to configure the laser depilating apparatus. When the plurality of semiconductor lasers 8 are used, the semiconductor lasers 8 are used in the number of, for example, 2 to 50. The laser depilating apparatus of this embodiment has 20 semiconductor lasers 8 as described later.

For the semiconductor lasers 8, laser diodes which emit laser beams having a wavelength in a range of, for example, 750 to 900 nm are used. The laser beams having a wavelength in a range of 750 to 900 nm provide favorable depilating effects because, for example, they relatively deeply penetrate the skin of a human body and are absorbed by melanin in a hair shaft and germinative cell with priority as compared with water or blood (hemoglobin). In other words, a laser beam having a wavelength of less than 750 nm is absorbed at a high rate by melanin but also absorbed substantially by blood or the like, possibly lowering utilization efficiency of a laser beam for depilating treatment and damaging the skin and the like. Meanwhile, when a laser beam has a wavelength of exceeding 900 nm, the absorption factor by melanin lowers, and a favorable depilating effect cannot be obtained. It is particularly desirable that the semiconductor laser beam has a wavelength in a range of 780 to 810 nm (800 nm as median).

The semiconductor laser 8 preferably has a power of 0.1 W or more. A semiconductor laser having a power of less than 0.1 W can be used, but the laser beam might not penetrate the skin sufficiently, though variable depending on the wavelength of such a low power semiconductor laser. Such a laser beam does not adequately reach the hair bulb and the like, so that a favorable depilating effect cannot be obtained, and hair might be restored depending on circumstances. The semiconductor laser 8 preferably has a power of 0.5 W or more, and more preferably 1 W or more, in order to penetrate the laser beam effectively into the skin.

But, if the semiconductor laser has an excessively high power, it is necessary to reduce an irradiation time of the laser beam, though variable depending on a spot size. Therefore, the thermal energy by the semiconductor laser beam might not be distributed over the entire hair follicle tissue. Therefore, the semiconductor laser 8 preferably has a power of 50 W or less. Thus, the present invention desirably uses the semiconductor laser 8 having a power in a range of 0.1 to 50 W. The semiconductor laser 8 has more preferably a power in a range of 0.5 to 10 W, and still more preferably in a range of 1 to 10 W.

The spot size (laser radiation area of one semiconductor laser 8) of each semiconductor laser 8 is ideally about 2 to 4 times of a penetration depth of the laser beam. It is necessary to consider the power of the semiconductor laser 8, but it is desirable in practice that an irradiation area of a laser beam by the semiconductor laser 8 is set to a range of 0.5 to 20 mm$^2$. The spot size (laser radiation area) of each semiconductor laser 8 is desirably set to a range of 0.5 to 10 mm$^2$, and more desirably in a range of 0.7 to 8 mm$^2$.

The plurality of semiconductor lasers 8, 8 . . . are held by a holding member 9 having a substantially spherical laser holding surface. Lenses (e.g., spherical lenses) 10, 10 . . . are respectively disposed in front of radiation by the plurality of semiconductor lasers 8, 8 . . . . The laser beams emitted by the individual semiconductor lasers 8 are focused on a radiating head 11 through the individual lenses 10. The radiating head 11 is made of, for example, quartz glass and makes a substantial contact with a skin surface which is subject to the laser depilating treatment.

The radiating head 11 has a light path therein to guide the individual semiconductor laser beams to a prescribed treatment region of a skin surface. The front face of the radiating head 11 is a laser irradiation surface 12. The individual laser beams emitted from the plurality of semiconductor lasers 8, 8 . . . are focused into the radiating head 11 by the lenses 10, 10 . . . . The individual semiconductor laser beams are determined to have light paths so to pass through prescribed portions in the radiating head 11 and shaped to have a spot size suitable for the laser depilation within the radiating head 11. The individual light paths in the radiating head 11 are set to radiate a substantially entire region of the laser irradiation surface 12 with the semiconductor laser beams. Therefore, the plurality of semiconductor laser beams are radiated to a skin surface corresponding to the area of the laser irradiation surface 12.

A relationship between the state of holding the plurality of semiconductor lasers 8, 8 . . . and the irradiation region of the plurality of semiconductor laser beams will be described in further detail. The laser depilating apparatus of this embodiment has, for example, 20 semiconductor lasers 8, 8 . . . . These 20 semiconductor lasers 8, 8 . . . are basically disposed in the shape of a matrix with 5 rows and 4 columns.

The holding member 9 for holding these 20 semiconductor lasers 8, 8 . . . has a laser holding surface which is spherical in the vertical sectional direction in FIG. 3 and circumflex in the transverse sectional direction in FIG. 4. The 20 semiconductor lasers 8, 8 . . . are set by the holding member 9 to have optical axes so that rays of light are gathered into the radiating head 11. The 20 semiconductor lasers 8, 8 . . . are held by the holding member 9 having the above-described laser holding surface in such a way that a distance from the each light emitting point to the light-gathering point in the radiating head 11 becomes substantially constant.

Meanwhile, the radiating head 11 has a rectangular laser irradiation surface 12. The laser irradiation surface 12 has a shape of, for example, 15×12 mm. In other words, the radiating head 11 has a laser radiation area of 15×12 mm (area=180 mm$^2$). The area of the laser irradiation surface 12 can be set appropriately according to the disposed number of semiconductor lasers 8, the contents of treatment and the like. When one semiconductor laser is used, its spot size becomes a laser radiation area. When a plurality of semiconductor lasers are used, the laser irradiation surface 12 preferably has an area of 15 mm$^2$ or more, and more preferably 50 mm$^2$ or more.

The semiconductor laser beams emitted from the individual semiconductor lasers 8 are formed to have prescribed spot sizes according to gathering of light according to the individual lenses 10, refraction at the time of incidence to the radiating head 11 and a length of light path by the radiating head 11. Besides, the individual semiconductor laser beams are set to have light paths so to pass through prescribed portions in the radiating head 11 depending on the shape of the holding member 9, the state of holding the semiconductor lasers 8 by the holding member 9, a positional relationship between the semiconductor lasers 8 and the radiating head 11, and the like. The individual light paths are determined in such a way that the semiconductor laser beams respectively irradiate substantially different regions in the laser irradiation surface 12, and the entire region of the laser irradiation surface 12 is substantially irradiated with the semiconductor laser beams.

Figure 5:
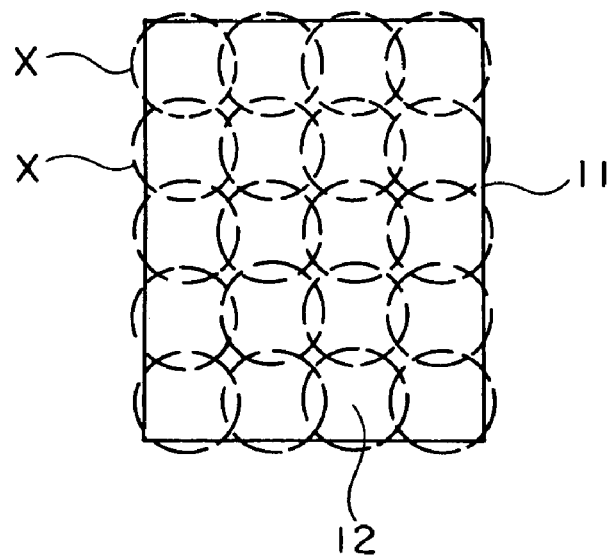
FIG. 5 is a view showing an irradiating state of a plurality of semiconductor laser beams in a laser irradiation surface of the laser radiating probe shown in FIG. 2.

As shown in FIG. 5, a plurality of semiconductor laser beams X, X . . . are configured to have light paths so to irradiate substantially different regions in the laser irradiation surface 12. The irradiation positions in the laser irradiation surface 12 by the plurality of semiconductor laser beams X, X . . . are in a matrix with 5 rows and 4 columns according to the number of semiconductor lasers 8 so to cover a substantially entire region of the laser irradiation surface 12. And, the rectangular laser irradiation surface 12 is substantially irradiated its entire region with the plurality of semiconductor laser beams X, X . . . .

The state of irradiation of the substantially different regions in the laser irradiation surface 12 with the plurality of semiconductor laser beams X, X . . . is adequate when the individual semiconductor laser beams X have at least different irradiation centers, and the neighboring semiconductor laser beams X may have somewhat overlapped irradiation ranges. The state that the entire region of the laser irradiation surface 12 is substantially irradiated with the plurality of semiconductor laser beams X, X . . . may be a state that it provides a depilating effect on the entire skin surface equivalent to the area of the laser irradiation surface 12 with the semiconductor laser beams X. There may be a small gap formed between the irradiation ranges of the neighboring semiconductor laser beams X, and even in such a case, the depilating effect can be provided by irradiation heat of the semiconductor laser beams X.

The plurality of semiconductor laser beams X, X . . . each have a substantially constant power density. Therefore, the laser beams having a substantially constant power density are collectively irradiated to the laser irradiation surface 12 of the radiating head 11. A skin surface is irradiated with the semiconductor laser beams X depending on the area of the rectangular laser irradiation surface 12, so that the laser beams having a substantially constant power density are collectively irradiated into the treatment region of the skin surface. The laser irradiation surface 12 (irradiation area: 180 mm$^2$) of the laser depilating apparatus of this embodiment has a shape of, for example, 15×12 mm. Therefore, a skin surface having substantially the same area can be irradiated with the semiconductor laser beams X collectively. By the laser depilating apparatus of this embodiment, it is possible to expand the region of depilating treatment per laser irradiation according to the irradiation state with the plurality of semiconductor laser beams X, X . . . .

A plurality of cooling air nozzles 13 are formed around the radiating head 11 of the laser radiating probe 4. Cooling air is supplied before, simultaneously with or after irradiation with the semiconductor laser beams. The temperature of the skin also rises slightly when the skin surface is irradiated with the semiconductor laser beams, but damage to the skin can be retarded more securely by blowing cooling air to the skin surface when irradiated with the semiconductor laser beams. Cooling gel or the like may also be used when irradiated with the semiconductor laser beams.

In the laser depilating apparatus of the above embodiment, a skin surface is irradiated with the semiconductor laser beams for an irradiation time of 100 msec or more per one time of irradiation while controlling an energy density to a range of 0.01 to 1 J/mm$^2$ when the skin surface of a human body subject to the depilating treatment is irradiated. When the skin surface is irradiated with the semiconductor laser beams, an energy density E is controlled by at least one of an irradiation time T and a power density L of the semiconductor laser beams. The above irradiation conditions of the semiconductor laser beams satisfy a relationship of an energy density E [J/mm$^2$]=power density L [W/mm$^2$]× irradiation time T [sec]. Therefore, the energy density is controlled to a desired range by adjusting the irradiation time T and/or the power density L of the semiconductor laser beams.

In practice, the power density L of the laser beams by the semiconductor lasers 8 is preferably determined to fall in a range of 0.01 to 5 W/mm$^2$ depending on the irradiation time T. If the power density L of the semiconductor laser beams in the irradiation region is less than 0.01 W/mm$^2$, an adequate depilating effect might not be obtained even if the irradiation time per irradiation of the semiconductor lasers 8 is extended. Meanwhile, when the semiconductor laser beams have a power density L of exceeding 5 W/mm$^2$, the irradiation time per one time cannot be determined to be long enough, and the thermal energy might not be distributed to cover the entire hair follicle tissue. It is desirable that the power density L of the semiconductor laser beams is set to a range of 0.05 to 2 W/mm$^2$.

The power density L of the semiconductor laser beams is determined according to power C of the semiconductor lasers 8 and spot size S of the semiconductor laser beams. In other words, it meets the relationship of power density L [W/mm$^2$]=power C [W]/spot size S [mm$^2$]. The spot size S is basically determined to be constant, so that the power density L of the semiconductor laser beams is controlled according to the power C of the semiconductor lasers 8. The output (light output) C of the semiconductor lasers 8 is controlled by a voltage value or current value input to the semiconductor laser (laser diode) 8.

The light output of the semiconductor laser beams can also be controlled by, for example, varying the on-time of the laser pulse with the semiconductor lasers 8 as pulse oscillation. But, the pulsed semiconductor laser beam cannot convey the thermal energy to the entire hair follicle tissue efficiently. The semiconductor lasers 8 are desired to be continuously oscillated in order to enhance the transmission efficiency of the thermal energy. Therefore, the light output of the semiconductor lasers 8 is controlled by the voltage value or current value input to the semiconductor lasers 8.

Figure 6:
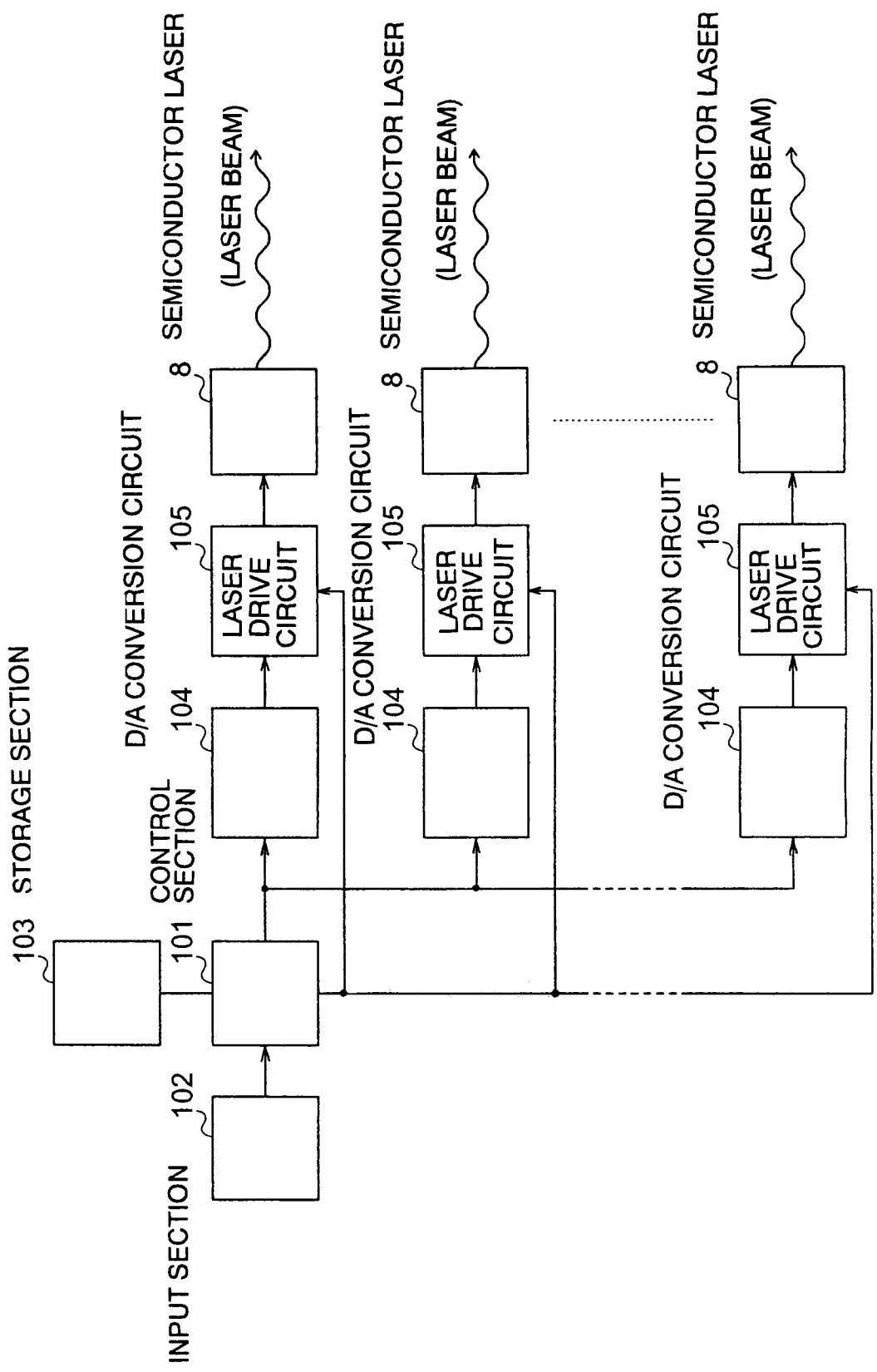
FIG. 6 is a block view showing a structure of a drive control section of a semiconductor laser of the laser depilating apparatus shown in FIG. 1.

FIG. 6 is a block view showing a structure of the drive control section of the semiconductor lasers 8. A control section 101 reads control signals for the drive conditions (voltage or current value) and drive time (laser beam irradiation time) of the semiconductor lasers 8 from a storage section 103 according to a treatment mode or the like input from an operation section 102. Among the control signals read from the storage section 103, the drive condition signal for the semiconductor lasers 8 is sent from the control section 101 to a laser drive circuit 105 via a D/A conversion circuit 104. The drive time signal for the semiconductor lasers 8 is sent from the control section 101 to the laser drive circuit 105.

According to the control signal, the laser drive circuit 105 inputs a prescribed voltage value or current value from an unshown laser drive power supply to the semiconductor lasers 8. Time of applying an input current is controlled by the laser drive circuit 105 according to the control signal. Thus, the power C and drive time (a laser beam irradiation time T) of the semiconductor lasers 8 are controlled. The spot size S of the semiconductor laser beams is basically determined to be constant, so that the power density L of the semiconductor laser beams is controlled by the power C of the semiconductor lasers 8.

The drive time (laser beam irradiation time T) of the semiconductor lasers 8 is set to 100 msec or more. After meeting the above condition, energy density E at the irradiation of a skin surface with the semiconductor laser beams is controlled according to the power density L and the irradiation time T of the semiconductor laser beams. The irradiation energy density E of the semiconductor laser beams is specifically controlled to a range of 0.01 to 1 $J/mm^2$. And, a skin surface is irradiated with the semiconductor laser beams having the above irradiation time T and irradiation energy density E to perform the depilating treatment by conveying the thermal energy based on the irradiation of the semiconductor laser beams to the entire hair follicle tissue.

Figure 7:
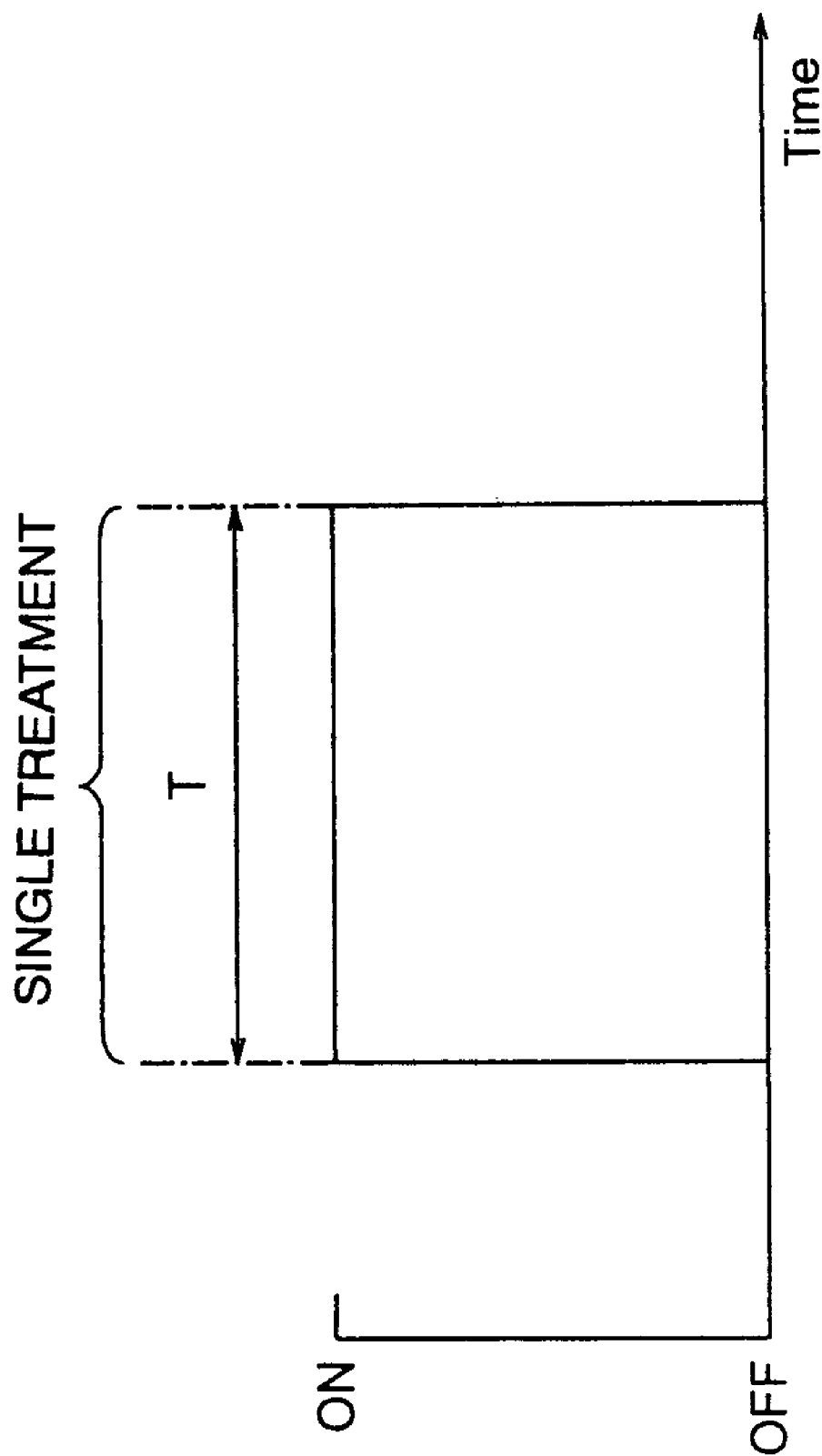
FIG. 7 is a view illustrating an irradiation time of a semiconductor laser beam according to one embodiment of the present invention.

It is important that a treatment region of the skin surface is irradiated with the semiconductor laser beams for an irradiation time of 100 msec or more per irradiation. Here, the irradiation time per irradiation of the semiconductor laser beam is a lighting time (ON-time) T per treatment by the semiconductor laser 8 as shown in FIG. 7. The semiconductor lasers 8 are basically driven by continuously oscillating, so that the irradiation time per irradiation of the semiconductor laser beam corresponds to the irradiation time per treatment.

Figure 8:
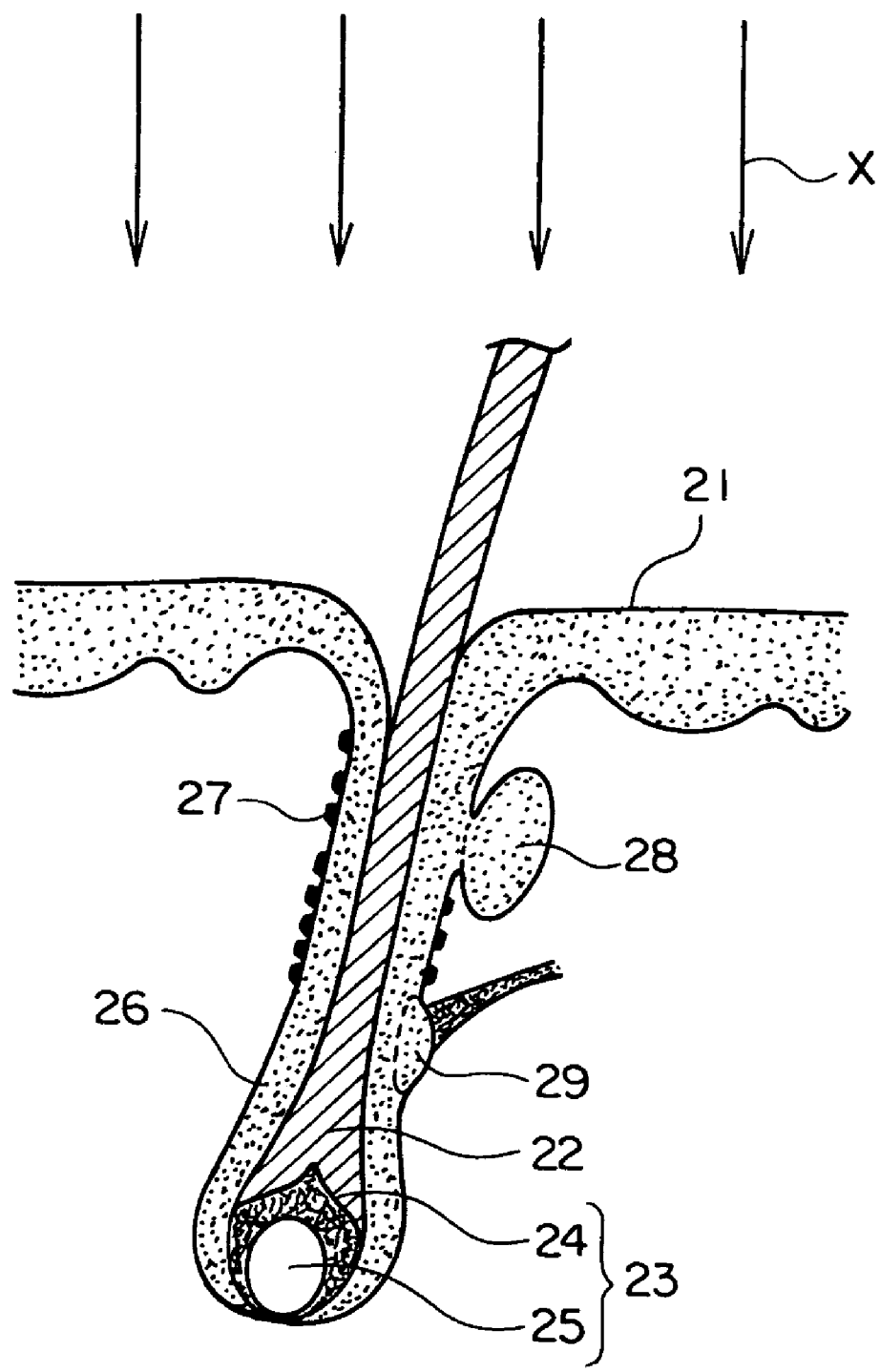
FIG. 8 is a view illustrating a state of body hair which is a target of laser depilating treatment.

As described above, the thermal energy of the laser beams absorbed by melanin in the hair shaft and germinative cell can be conducted to the entire hair follicle tissue by irradiating a skin surface with the semiconductor laser beams determined to have the irradiation time T of 100 msec or more per irradiation. Specifically, when a skin surface 21 is irradiated with the semiconductor laser beams X with the irradiation time T set to 100 msec or more per irradiation as shown in FIG. 8, the semiconductor laser beams X penetrate the skin and are selectively absorbed by melanin contained in a hair shaft 22 and a germinative cell 24 of a hair bulb 23. The hair shaft 22 and the germinative cell 24 having selectively absorbed the semiconductor laser beams X are heated to a prescribed temperature of, for example, about 60 to 100° C. by the thermal energy of the semiconductor laser beams X.

At this time, the irradiation time T of the semiconductor laser beams X per irradiation is set long to be 100 msec or more. Therefore, the thermal energy absorbed by the melanin in the hair shaft 22 and the germinative cell 24 is sufficiently propagated to their peripheries. Accordingly, the hair shaft 22, the germinative cell 24 and a hair papilla 25, and the entire hair follicle tissue including a sheath 26 as connective tissue around them, a stem tissue 27, a sebaceous gland 28 and a bulge 29 can be heated securely and efficiently to a temperature effective for depilating. A region having a temperature of approximately 60 to 100° C. which is considered to be effective for depilating is approximately equal to or larger than a diameter of the hair follicle, and thermal damage is applied to a region having such a temperature.

As described above, when the semiconductor laser beam X is determined to have the irradiation time T of 100 msec or more per irradiation, the thermal damage can be given effectively and securely to the entire hair follicle tissue. And, the regrowth of hair can be retarded surely by applying thermal damage to the entire hair follicle tissue, namely not only the hair shaft 22 and the germinative cell 24 but also the sheath 26 as the connective tissue and the stem tissue 27, the sebaceous gland 28 and the bulge 29 with the semiconductor laser beams X. In other words, the depilating effects based on the hair growth retarding effect and the reducing effect can be obtained securely and efficiently. In addition, the depilating treatment can be performed safely because the skin can be prevented from having a high temperature.

Meanwhile, when the semiconductor laser beam has an irradiation time T of less than 100 msec per irradiation, the thermal energy is not conducted sufficiently by the semiconductor laser beams having the same power density as above, and thermal damage cannot be given adequately to the entire hair follicle tissue. When the power density of the semiconductor laser beams is increased to a level capable of attaining the depilating effects, the hair shaft 22 and the germinative cell 24 are excessively heated to cause a thermally insulated state and suffer from decomposition and vaporization. It means that the absorber for the semiconductor laser beams is lost, and a temperature is caused to drop by the heat of vaporization. Thus, the thermal damage cannot be given effectively to the entire hair follicle tissue. Besides, the skin temperature might become high, and a side effect might be caused as a result.

The irradiation time T per irradiation of the semiconductor laser beams can be set appropriately to a range of retarding the skin from having a high temperature or damage resulting from it but preferably set to 10 sec or less in view of practical use. The irradiation time T per irradiation of the semiconductor laser beams is preferably set to 100 msec or more and 10 sec or less. Besides, the irradiation time T per irradiation of the semiconductor laser beams X is particularly desired to be in a range of 1 to 5 sec considering the laser depilating effect and safety.

Not only the irradiation time T per irradiation of the semiconductor laser beam but also the energy density E of the semiconductor laser beam are pertinent to the laser depilating effect. Specifically, even if the irradiation time T per irradiation of the semiconductor laser beam is set to be long, the thermal damage cannot be given efficiently to the entire hair follicle tissue when the energy density E of the semiconductor laser beam is excessively low. Therefore, the energy density E of the semiconductor laser beam is controlled to a range of 0.01 to 1 $J/mm^2$ while keeping the irradiation time T per irradiation of the semiconductor laser beam to 100 msec or more.

As described above, the energy density E and the irradiation time T satisfy the relationship of the energy density E $[J/mm^2]$=power density L $[W/mm^2]$×irradiation time T [sec]. Therefore, the energy density E of the semiconductor laser beams is controlled to a range of 0.01 to 1 $J/mm^2$ by adjusting the irradiation time T and the power density L of the semiconductor laser beams while the irradiation time T per irradiation of the semiconductor laser beam is kept to 100 msec or more. When the semiconductor laser beams having the energy density E are used, it is possible to conduct the thermal energy having a high depilating effect to the entire hair follicle tissue securely and efficiently.

When the energy density E of the semiconductor laser beams is less than 0.01 $J/mm^2$, the thermal damage cannot be given to the entire hair follicle tissue. Meanwhile, when the energy density E exceeds 1 $J/mm^2$, the hair shafts and germinative cells might be decomposed, the skin might have a high temperature, and a side effect might be caused as a result. The energy density E of the semiconductor laser beam is especially desired to be controlled to a range of 0.1 to 0.4 $J/mm^2$. This irradiation energy density E can give thermal damage to the hair follicle tissue more effectively.

As described above, the thermal damage can be caused effectively and securely to the entire hair follicle tissue with the semiconductor laser beam which is set to have the irradiation time T of 100 msec or more per irradiation and the irradiation energy density E controlled to a range of 0.01 to 1 J/mm². Thus, an effect of retarding the growth of hair and an effect of lowering it can be obtained securely and efficiently. Specifically, it becomes possible to obtain the laser depilating effects securely and efficiently by making use of a feature of the semiconductor laser beam that the absorption efficiency by melanin in hair shafts and germinative cells is high. In addition, the depilating treatment can be performed safely because the skin temperature does not become high.

Besides, the laser depilating apparatus of this embodiment emits the laser beams having a substantially constant power density from the laser irradiation surface 12 of the radiating head 11 by gathering the plurality of laser beams emitted from the plurality of semiconductor lasers 8, 8 . . . and forming. An irradiation range (irradiation area) of the semiconductor laser beams having the substantially constant power density is substantially expanded, so that the depilating treatment can be performed on a large region by a single laser irradiation. Therefore, it is possible to enhance a depilating treatment speed extensively without lowering the depilating effects by the semiconductor laser beams.

Especially, the laser depilating apparatus of this embodiment has the plurality of semiconductor lasers 8, 8 . . . disposed in a matrix with m rows and n columns and irradiates the rectangular laser irradiation surface 12 with the plurality of semiconductor laser beams corresponding to the disposed state. The entire region of the rectangular laser irradiation surface 12 is irradiated with the semiconductor laser beams having the substantially constant power density collectively, so that a region which can be treated by a single laser irradiation can be enlarged substantially as compared with an existing laser depilating apparatus having a plurality of semiconductor lasers disposed in a circular form. Besides, the depilating effect in the enlarged laser irradiation region can be enhanced more uniformly.

Specific laser depilating treatment is performed by first shaving hair on a skin surface and applying cooling gel or the like to the treatment region. In the laser depilating treatment process, the treatment time is set to, for example, 5 to 60 minutes, and the semiconductor laser beams are repeatedly irradiated and suspended within the treatment time. The semiconductor laser beams are irradiated while gradually moving their positions on the skin surface. The irradiation time of the semiconductor laser beams is determined as a lighting time per irradiation as described above. While the irradiation of the semiconductor laser beams is being suspended, cooling air is blown from the air nozzles 13 to the skin surface to retard the temperature increase of the skin. Thus, the depilating treatment is performed.

The laser depilating apparatus of this embodiment was used to actually perform the laser depilating treatment to find that a favorable depilating effect could be obtained by irradiating the lasers under the above-described conditions. Specifically, the laser depilating treatment was performed by irradiating a leg of a subject with the semiconductor laser beams (800 nm as median) with the irradiation time T set to 3 sec per irradiation while controlling the semiconductor laser beams to have an energy density in a range of 0.1 to 0.4 J/mm² at the time of the irradiation. The laser depilating treatment was performed for eight weeks. The laser treatment was performed two times a week for the first four weeks and one time a week for the next four weeks. It was confirmed as a result that plural subjects had favorable depilating effects (reduction in number of hair, reduction in hair shaft diameter (thin hair), decrease of pigment in hair, etc.).

Meanwhile, as a comparative example of the present invention, the irradiation time T of the semiconductor laser beams was lowered to 40 msec per irradiation with the same power of the semiconductor lasers to perform the same treatment for eight weeks as the above-described embodiment to find that favorable depilating effects could not be obtained. Besides, when the irradiation time T of the semiconductor laser beams was set to 40 msec per irradiation and the irradiation energy density was controlled to a range of 0.1 to 0.4 J/mm², the favorable depilating effects could not be obtained either.

As described above, it is possible to obtain the laser depilating effects more securely and efficiently by utilizing the features of the semiconductor laser beams that the absorption efficiency by melanin in hair shafts and germinative cells is high by the laser depilating apparatus and the laser depilating treatment using it of this embodiment. In the above-described embodiment, the use of the plurality of semiconductor lasers was described, but the invention is not limited to it and can also be applied to a laser depilating apparatus using a single semiconductor laser.

In addition, all the plurality of semiconductor lasers 8, 8 . . . are not required to come on during the treatment, and only desired semiconductor lasers may be lit depending on a treatment area, a shape of treatment region and the like. FIG. 9 is a block view showing a structure of the laser drive control section according to another embodiment of the invention. The laser depilating apparatus of this embodiment sends a drive time signal for the semiconductor laser 8 from the control section 101 to the laser drive circuit 105 via a switch circuit 106. A control signal is sent from the control section 101 to the switch circuit 106 to turn on the switch of the semiconductor lasers so to light among the plurality of semiconductor lasers 8, 8 . . . .

Thus, the laser beams can be emitted from only desired semiconductor lasers among the plurality of semiconductor lasers 8, 8 . . . . Selection of desired semiconductor lasers enables to change a laser depilating treatment area. This configuration is effective in changing a treatment area or a treatment portion by a single laser radiating probe 4.

INDUSTRIAL APPLICABILITY

According to the laser depilating method and laser depilating apparatus of the present invention, it becomes possible to obtain the depilating effects more securely and efficiently by utilizing the feature of the semiconductor laser beams that an absorption efficiency by melanin in hair shafts and germinative cells is high. Such a laser depilating method and laser depilating apparatus are effectively used for various kinds of depilating treatments. Besides, a treatment region can be increased by using a plurality of semiconductor lasers, and it becomes possible to enhance a depilating treatment speed.

What is claimed is:

1. A laser depilating apparatus, for retarding a regrowth of hair comprising:

a semiconductor laser for emitting a laser beam having a wavelength in a range of 750 to 900 nm and a power density in a range of 0.01 to 5 W/mm²;

a radiating head having a light path for guiding the laser beam and a laser irradiation surface so as to irradiate a skin surface subject to depilating treatment with the laser beam emitted from the semiconductor laser; and an irradiation condition control section for controlling an irradiation time of the laser beam to 100 msec or more per irradiation and an energy density to a range of 0.01 to 1 J/mm$^2$, and configured such that an entire hair follicle tissue of the skin surface is heated to a temperature greater than 60° C. and less than 100° C. so that the regrowth of hair can be retarded through thermal damage to the entire hair follicle tissue when the skin surface is irradiated with the laser beam.

2. The laser depilating apparatus according to claim 1, wherein the irradiation condition control section controls at least one selected from the irradiation time and the power density of the laser beam to make the laser beam having the energy density in the range of 0.01 to 1 J/mm$^2$.

3. The laser depilating apparatus according to claim 2, wherein the irradiation condition control section controls the irradiation time of the laser beam to the range of 100 msec or more and 10 sec or less per irradiation.

4. The laser depilating apparatus according to claim 1, wherein the laser beam has the wavelength in the range of 780 to 810 nm.

5. The laser depilating apparatus according to claim 1, wherein the semiconductor laser is one of a plurality of semiconductor lasers, the laser depilating device further comprising:
an optical system for gathering and forming a plurality of laser beams emitted from the plurality of semiconductor lasers so as to have the entire region of the laser irradiation surface of the radiating head substantially irradiated with the laser beams.

6. The laser depilating apparatus according to claim 5, wherein the radiating head has the laser irradiation surface in a rectangular shape, and the plurality of semiconductor lasers are disposed to respectively irradiate substantially different regions in the rectangular laser irradiation surface with the plurality of laser beams.

7. The laser depilating apparatus according to claim 6, wherein the plurality of semiconductor lasers are supported by a member having a spherical holding surface so as to have substantially constant distances from individual light emitting points to a light-gathering point in the radiating head.

8. The laser depilating apparatus according to claim 5, further comprising:
a laser switching section for emitting the laser beam from any semiconductor laser among the plurality of semiconductor lasers.

9. The laser depilating apparatus according to claim 1, wherein the irradiation condition control section controls the irradiation time of the laser beam to 1 sec or more.

10. The laser depilating apparatus according to claim 1, wherein the hair follicle tissue includes a hair shaft, a germinative cell, a sheath as connective tissue, a stem tissue, a sebaceous gland and a bulge.

11. The laser depilating apparatus according to claim 10, wherein the laser beam with the irradiation time of 100 msec or more per irradiation is absorbed by the hair shaft and the germinative cell, and the thermal energy of the laser beam absorbed by the hair shaft and the germinative cell is propagated to the hair follicle tissue so that the thermal damage is applied to the entire hair follicle tissue.

12. The laser depilating apparatus according to claim 1, wherein the irradiation time of the laser beam corresponds to the irradiation time per treatment for depilating.

* * * * *